United States Patent [19]
Wild et al.

[11] 3,947,405
[45] Mar. 30, 1976

[54] PROCESS FOR MAKING NEOHESPERIDINE DIHYDROCHALCONE

[75] Inventors: Jost Wild, Uster; Ulrich Huber, Zurich, both of Switzerland

[73] Assignee: Givaudan Corporation, Clifton, N.J.

[22] Filed: Dec. 18, 1974

[21] Appl. No.: 534,048

[30] Foreign Application Priority Data
Jan. 3, 1974 Switzerland............................... 8/74
Nov. 6, 1974 Switzerland....................... 14840/74

[52] U.S. Cl............................................. 260/210 F
[51] Int. Cl.²......................................... C07H 17/04
[58] Field of Search................................. 260/210 F

[56] References Cited
UNITED STATES PATENTS

| | | | |
|---|---|---|---|
| 3,375,242 | 3/1968 | Horowitz et al................. | 260/210 F |
| 3,522,236 | 7/1970 | Krbechek et al................ | 260/210 F |

Primary Examiner—Johnnie R. Brown
Attorney, Agent, or Firm—Thomas Cifelli, Jr.

[57] ABSTRACT

The known sweetening agent, neohesperidin dihydrochalcone is manufactured by reacting phloroacetophenone-4'-β-neohesperidoside with isovanillin in the presence of a secondary amine and an organic acid in solution to give neohesperidin or its chalcone and then hydrogenating the reaction product in a manner known per se.

8 Claims, No Drawings

PROCESS FOR MAKING NEOHESPERIDINE DIHYDROCHALCONE

FIELD OF THE INVENTION

This invention relates to the field of sweetening agents.

SUMMARY OF THE INVENTION

The known sweetening agent, neohesperidin dihydrochalcone is manufactured by reacting phloroacetophenone-4'-β-neohesperidoside with isovanillin in the presence of a secondary amine and an organic acid in solution to give neohesperidin or its chalcone and then hydrogenating the reaction product in a manner known per se.

DESCRIPTION OF THE PREFERRED EMBODIMENTS

Examples of secondary amines which can be used in the present process are aliphatic amines such as di(-lower alkyl)amines (e.g. dimethylamine, diethylamine, diisopropylamine etc), aliphatic-aromatic amines such as lower alkylarylamines (e.g. methylphenylamine), diaromatic amines (e.g. diphenylamine etc), alkanolamines (e.g. diethanolamine etc) and, especially, cyclic amines (e.g. morpholine, piperidine, pyrrolidine and piperazine). Pyrrolidine is preferred.

As the organic acid there is preferably used a carboxylic acid such as a lower alkanecarboxylic acid (e.g. acetic acid, propionic acid etc), formic acid or an aromatic carboxylic acid (e.g. benzoic acid etc). Acetic acid is preferably used.

Whether the reaction of phloroacetophenone-4'-β-neohesperidoside (neohesperidosylacetylphloroglucinol, acetylphloroglucinol neohesperidoside) of the formula

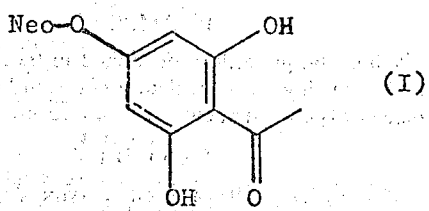

(I)

wherein Neo represents the β-neohesperidosyl group, i.e. the 2-O-α-L-rhamnopyranosyl-β-D-glucopyranosyl group of the formula

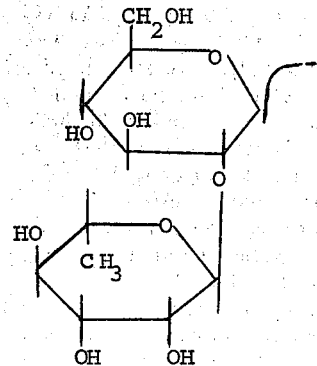

with isovanillin yields mainly neohesperidin (II) or its chalcone (III)

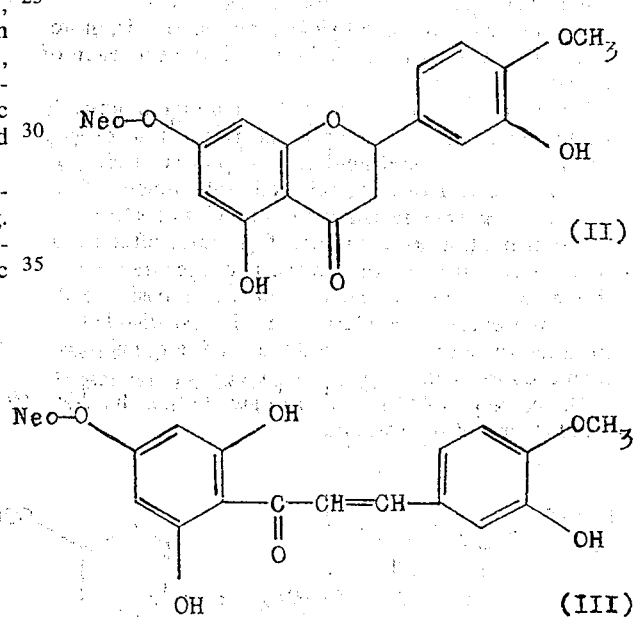

depends on the ratio of secondary amine to organic acid used in the process. When this ratio is 1:1, i.e. the reaction medium is neutral (or weakly acid), neohesperidin (II) is mainly or almost exclusively obtained. When the reaction medium is basic, i.e. the secondary amine is present in excess, the chalcone (III), which represents the primary reaction product of the compound of formula I with isovanillin, is mainly obtained. The duration of the reaction also has an influence on the ratio of neohesperidin (II) to chalcone (III) obtained. The longer the duration, the more of neohesperidin (II) is obtained.

The ratio of the compound of formula I to isovanillin is preferably 1:1, but a slight excess (e.g. 5%) of the individual reaction components does not give rise to any disadvantages. The reaction is carried out in solution. The secondary amine, as long as it is liquid under the reaction conditions, or a polar organic solvent can be used as the solvent. Examples of such solvents which can be used are: alcohols such as alkanols (e.g. methanol, ethanol etc), polyalcohols (e.g. glycols or glycerine), ethers (e.g. dioxane, methylal etc), polyethyleneglycol ethers [e.g. diethyleneglycol ethers such as mono- and diglyme (diethyleneglycol monomethyl or dimethyl ether)], tertiary amines (e.g. pyridine, triethylamine etc), dimethylformamide, dimethyl sulphoxide, N-methylpyrrolidone, hexamethylphosphoric acid triamide and the like. Ethanol and isopropanol are preferred solvents.

The ratio of secondary amine to compound of Formula I can be varied within a wide range; for example, between 100:1 and 1:100 (equivalent). However, the ratio preferably lies within a range of 5:1 and 1:20.

The temperature at which the reaction is carried out can be varied within wide limits; for example, the reaction can be carried out at a temperature between room temperature and the boiling point of the reaction mixture. A temperature of 40°–100°C is preferred.

The reaction is preferably carried out in an inert atmosphere (e.g. under nitrogen, argon etc).

In order to obtain good yields, the reaction is, moreover, advantageously carried out with the exclusion of moisture.

When the reaction is carried out under practically neutral conditions (i.e. when the ratio of secondary amine to organic acid amounts to approximately 1:1) — which represents the preferred embodiment of the process — racemic neohesperidin precipitates from the reaction mixture in crystalline form and, after filtration, can be used directly in the hydrogenation stage. When the reaction is carried out under basic conditions, the excess secondary amine is first distilled off from the reaction mixture and the residue remaining is then used in the hydrogenation stage.

The catalytic hydrogenation to give hesperidin dihydrochalcone of the formula

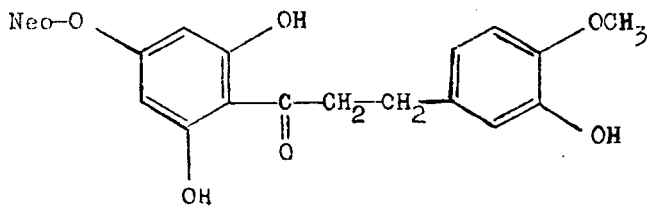

(IV)

can be carried out in a manner known per se. A suitable catalyst is, for example, Raney-nickel. The catalytic hydrogenation is expediently carried out in a solvent (e.g. water or an alkanol such as methanol) and at room temperature.

The following Examples illustrate the present invention:

EXAMPLE 1

2.4 g (0.005 mol) of acetylphloroglucinol neohesperidoside, 25 ml of absolute ethanol, 1.07 g (0.015 mol) of pyrrolidine, 0.23 g of acetic acid and 0.76 g (0.005 mol) of isovanillin are heated at reflux for 1 hour under an argon atmosphere. The mixture is then carefully concentrated on a rotary evaporator and the residual pyrrolidine removed under a high vacuum. The deep-red crystal mass obtained is taken up in 20 ml of 1-N sodium hydroxide, the solution washed three times with 20 ml of methylene chloride each time, purified with active carbon and filtration over Celite (rinsing with water) and 0.5 g of wet Raney-nickel is added to the filtrate. The mixture is hydrogenated for 12 hours, during which time approximately 1 equivalent of hydrogen is taken up. The catalyst is filtered off over Celite and the filtrate adjusted to pH 5 with 4 ml of 5-N hydrochloric acid while cooling. The excess isovanillin is removed by washing with two 20 ml portions of ether. The aqueous phase is extracted for 21 hours in a Kutscher-Steudel extractor using ethyl acetate/ethanol (80:20). The extract is concentrated and dried in a high vacuum. The yield is 2.5 g (82% of theory). The product shows a single spot on a polyamide thin-layer plate [eluant: nitromethane/methanol/water (60:37:3)] which corresponds to neohesperidin dihydrochalcone.

EXAMPLE 2

24 g (0.050 mol) of dried acetylphloroglycinol neohesperidoside are suspended in 250 ml of 99.8% ethanol and the suspension is treated with 3.55 g (0.005 mol) of pyrrolidine and 3 g (0.05 mol) of acetic acid. 7.6 g (0.050 mol) of isovanillin are added to the resulting mixture. The mixture is then maintained at reflux under an argon atmosphere with vigorous stirring for 12 hours. After cooling, the crystalline neohesperidin is filtered off under a vacuum and washed with 250 ml of ethanol. After drying in a high vacuum, 26.1 g (85% yield) of product of melting point 230°–240°C are obtained.

18.9 g (0.030 mol) of neohesperidin are dissolved in 90 ml of 2-N sodium hydroxide and treated with 1.2 g of Raney-nickel. The mixture is hydrogenated under normal pressure for 15 hours. The hydrogen uptake corresponds to 30 mmol. The solution is filtered and adjusted to pH 6 with 36 ml of 5-N hydrochloric acid while cooling with ice and stirring. The resulting clear yellow solution is left in a refrigerator for 48 hours and then filtered under suction. The white residue is washed with cold water and dried overnight in a high vacuum. There are obtained 17.4 g (95% yield) of neohesperidin dihydrochalcone of melting point 150°C.

EXAMPLE 3

When the procedure described in Example 2 is carried out using an equivalent amount of benzoic acid in place of the acetic acid, the same results are obtained.

EXAMPLE 4

47.6 g (0.10 mol) of dried acetylphloroglucinol neohesperidoside are suspended in 500 ml of isopropanol and treated with 7.1 g (0.10 mol) of pyrrolidine and 6 g (0.10 mol) of acetic acid. 15.2 g (0.10 mol) of isovanillin are added to the resulting mixture. The mixture thus obtained is maintained at reflux for 15 hours with vigorous stirring. After cooling, the crystalline neohesperidin is filtered off under suction and washed with 300 ml of ethanol. After drying in a vacuum, there are obtained 53 g (87% yield) of product of melting point 236°–238°C. The purity amounts to 92% according to high pressure liquid chromatography.

18.9 g (0.030 mol) of neohesperidin are dissolved in 90 ml of 2-N sodium hydroxide and treated with 1.2 g of Raney-nickel. The mixture is hydrogenated for 15 hours under normal pressure. The hydrogen uptake corresponds to 30 mmol. The solution is filtered and adjusted to pH 6 with 36 ml of 5-N hydrochloric acid while cooling with ice and stirring. The clear yellow solution is left in a refrigerator for 48 hours and then filtered under suction. The white residue is washed with cold water and dried overnight in a high vacuum. There are obtained 17.4 g (95% yield) of neohesperidin dihydrochalcone of melting point 150°C.

What is claimed is:

1. A process for the manufacture of neohesperidin dihydrochalcone, which process comprises reacting phloroacetophenone-4'-β-neohesperidoside with isovanillin in the presence of a secondary amine and an organic acid in solution to give neohesperidin or its chalcone and thereafter hydrogenating the reaction product, wherein the secondary amine is a member of the group selected from aliphatic amines such as di(-lower alkyl) amines (e.g. dimethylamine, diethylamine, diisopropylamine etc), aliphatic-aromatic amines such as lower alkylarylamines (e.g. methylphenylamine), diaromatic amines (e.g. diphenylamine etc), alkanolamines (e.g. diethanolamine etc) and, cyclic amines (e.g. morpholine, piperidine, pyrrolidine and piperazine) and wherein the organic acid is a member of the group selected from a carboxylic acid such as a lower alkanecarboxylic acid (e.g. acetic acid, propionic acid etc), formic acid or an aromatic carboxylic acid (e.g. benzoic acid etc).

2. A process according to claim 1, wherein the molar ratio of reactants phloroacetophenone-4'-β-neohesperidoside and isovanillin is about 1:1.

3. A process according to claim 1, wherein the molar ratio of secondary amine to organic acid lies within a range of about 5:1 and about 1:20.

4. A process according to claim 1, wherein the reaction between phloroacetophenone 4'-β-neohesperidoside and isovanillin is carried out at a temperature within the range from about 40°C. to about 100°C.

5. A process according to claim 1, wherein pyrrolidine is used as the secondary amine and acetic acid is used as the organic acid.

6. A process according to claim 1, wherein about 2.4 parts of phloroacetophenone 4'-β-neohesperiodoside about 0.76 parts of isovanillin, about 1.07 parts of pyrrolidine and about 0.23 parts of acetic acid are employed in ethanol as solvent and the reaction is conducted under reflux, the parts all being by weight, and using Raney-nickel as hydrogenation catalyst.

7. A process according to claim 1, wherein about 24 parts of phloroacetophenone 4'-neohesperidoside about 7.6 parts of isovanillin, about 3.55 parts of pyrrolidine and about 3 parts of acetic acid are employed in ethanol as solvent and the reaction is conducted under reflux, the parts being by weight, and using Raney-nickel as hydrogenation catalyst.

8. A process according to claim 1, wherein about 47.6 parts of phloroacetophenone-4'-β-neohesperidoside about 15.2 parts of isovanillin, about 7.1 parts of pyrrolidine and about 6 parts of acetic acid are employed in isopropanol as solvent, and the reaction is conducted under reflux, the parts being by weight, and using Raney-nickel as hydrogenation catalyst.

* * * * *